United States Patent [19]
Robbins et al.

[11] Patent Number: 5,683,487
[45] Date of Patent: Nov. 4, 1997

[54] HYDROPHOBIC BIOREMEDIANTS

[75] Inventors: Max Leo Robbins, South Orange; Ramesh Varadaraj, Flemington, both of N.J.

[73] Assignee: Exxon Research and Engineering Company, Florham Park, N.J.

[21] Appl. No.: 499,265

[22] Filed: Jul. 7, 1995

[51] Int. Cl.$^6$ .................. C05F 11/08; C02F 3/00
[52] U.S. Cl. .............. 71/6; 71/29; 71/903; 435/262; 210/610
[58] Field of Search ............... 71/1, 67, 11, 27, 71/28, 29, 33, 34, 64.1, 903; 210/610; 435/262

[56] References Cited

U.S. PATENT DOCUMENTS 4,933,000   6/1990   Somlo ........................... 71/93

Primary Examiner—Ferris Lander
Attorney, Agent, or Firm—Joseph J. Dvorak

[57] ABSTRACT

In one embodiment, the present invention provides a microbial nutrient composition comprises a stable, bi-continuous first and second phase. The first phase comprises an aqueous solution of microbial nutrients and the second phase comprising a hydrocarbon liquid and a mixture of surfactants combined in amounts sufficient to render the mixture of first and second phases a liquid at a first temperature and as a waxy solid at a lower second temperature.

In another embodiment of the present invention, there is provided a method for treating hydrocarbon contaminated soils and water by applying to the soil or water a microbial nutrient composition which is in the liquid state when it is applied and which forms a waxy solid at temperatures below the application temperature.

4 Claims, 1 Drawing Sheet

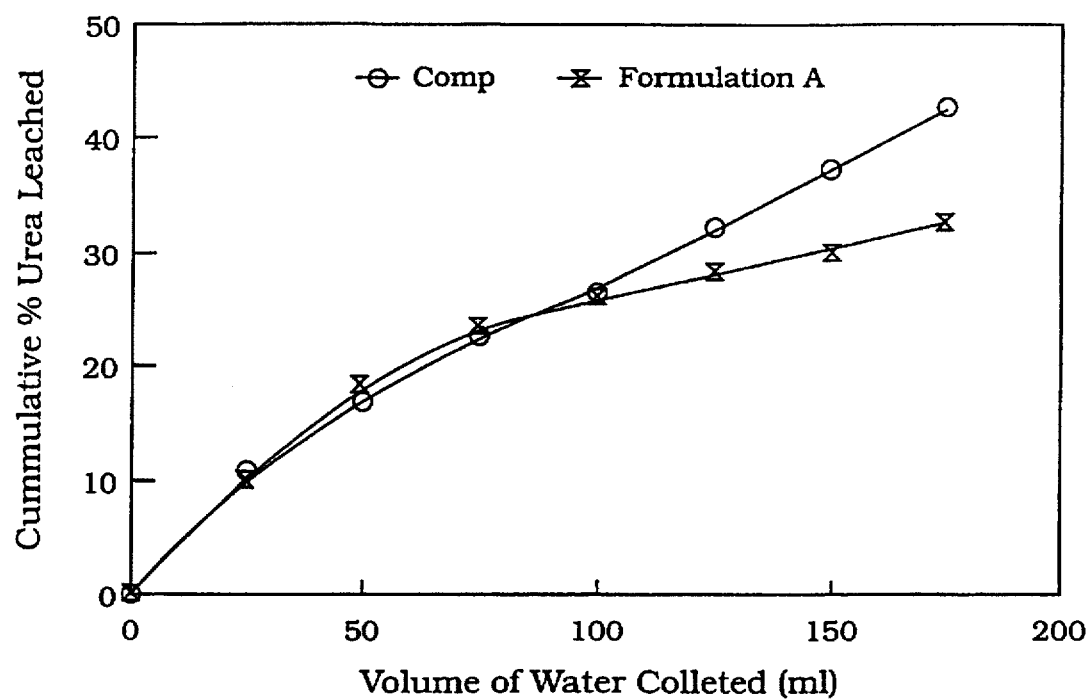

# HYDROPHOBIC BIOREMEDIANTS

FIELD OF THE INVENTION

The present invention relates to novel bioremediant compositions and their use in enhancing the microbial degradation of hydrocarbon contaminated soils and water.

BACKGROUND OF THE INVENTION

As is well-known there are several microbial species found in soil and water that are capable of assimilating petroleum hydrocarbons. Unfortunately, the rate of microbial assimilation of these petroleum hydrocarbons is relatively slow. It is necessary therefore to stimulate the microbial assimilation of the hydrocarbons if bioremediation is to be utilized as an efficient and practical technique in removing such pollutants from soil and water.

In general, the rate and extent of microbial utilization of petroleum hydrocarbons is limited by the concentration of microbial nutrients and micro flora available at the water hydrocarbon interface. Therefore, microbial nutrients, especially nitrogen containing nutrients like urea, have been added to contaminated to soil and water as a method for enhancing the biodegradation of the contaminants. Because these nitrogen containing microbial nutrients are generally water-soluble they tend to diffuse into the water or adjacent ground and consequently are not available in the immediate vicinity of the contaminant where a strong growth of microorganisms is desired. Thus, a number of techniques have been employed in an attempt to overcome this problem. For example, one technique employed is to coat solid nutrients with a material which is oleophilic so that the coated nutrients adhere to the hydrocarbon contaminate. Unfortunately, this type of coating does not permit the micro organism to have the nutrients available rapidly. Also, the solid granules of nutrient cannot be freely dispersed.

An alternate approach which avoids the use of solid nutrient substances involves the use of a micro emulsion of an aqueous solution of a nutrient material and a liquid immiscible with water. While this approach has the benefit of being able to be applied freely over a large area by spraying, nonetheless the nutrients do tend to diffuse over time in the water or in the adjacent ground.

There are, of course, other facets to the treatments of contaminated soils and water and many researchers have worked toward the discovering of more successful processes for improving the biodegradation of them.

It is an object of the present invention to provided novel compositions that have particular utility in enhancing microbial degradation of hydrocarbon contaminated soils and water.

It is another object of the present invention to provide a novel technique for maintaining microbial nutrients in contact with water or soil contaminants for extended periods of time.

SUMMARY OF THE INVENTION

In one embodiment, the present invention provides a microbial nutrient composition that comprises a stable, bi-continuous first and second phase. The first phase comprises an aqueous solution of microbial nutrients and the second phase comprises a hydrocarbon liquid and a mixture of surfactants combined in amounts sufficient to render the mixture of first and second phases a liquid at a first temperature and as a waxy solid at a lower second temperature.

In another embodiment of the present invention, there is provided a method for treating hydrocarbon contaminated soils and water by applying to the soil or water a microbial nutrient composition which is in the liquid state when it is applied and which forms a waxy solid at temperatures below the application temperature.

These and other embodiments of the present invention will become more apparent upon a reading of the detailed description which follows.

BRIEF DESCRIPTION OF THE DRAWINGS

The accompanying FIGURE compares urea leaching results obtained using formulation A of this invention with a commercially available liquid nutrient product.

DETAILED DESCRIPTION OF THE INVENTION

The present invention provides a novel approach to the supply of an aqueous solution of microbial nutrients to hydrocarbon contaminated soil and water in which the aqueous microbial nutrient solution is maintained in contact with the contaminants for an extended time period without substantial diffusion in the water or adjacent ground. Basically, the novel technique comprises applying to the contaminated soil or water a bioremediation composition which is a liquid at a first temperature but which forms a waxy solid at a second lower temperature. Compositions which meet this criteria constitute another aspect of the present invention.

The compositions of the present invention comprise a stable, bi-continuous first and second phase. The first phase in the compositions of the present invention comprise an aqueous solution of microbial nutrients. Typical microbial nutrients include ammonium nitrate, and/or phosphate, urea, proteins, and the like. Because urea is the richest source of nitrogen and is very soluble in water, it is particularly preferred to use urea in the compositions of the present invention. For example, aqueous solutions of urea containing from 10 to 60% by weight of urea the based on weight of the aqueous solution can be employed.

Phosphorus, which is another microbial nutrient, can also be provided in the solution in the form of phosphate or phosphate salts. Particularly preferred in the practice of the invention is the use of ammonium di-hydrogen phosphate. In general the aqueous solution will contain and from 0.1 to 10 weight % ammonium phosphate based on the weight of the aqueous solution. A particularly preferred solution of microbial nutrients includes urea and ammonium di-hydrogen phosphate in about a 5:1 weight ratio.

Optionally, the aqueous phase may also contain well-known microbial micro nutrients in appropriate amounts.

The second phase of compositions of the present invention comprises a hydrocarbon liquid that contains a mixture of surfactants combined in amounts sufficient to render a mixture of the first and the second phase a liquid at a first temperature and a waxy solid at a second temperature that is lower than the first temperature.

In the practice of the present invention, the hydrocarbon liquid preferably is a paraffinic solvent having a substantially high normal paraffin content and a relatively narrow boiling range. A particularly preferred hydrocarbon solvent is a normal paraffin solvent sold under the trade name Norpar® 13 by Exxon Company, USA, Houston, Tex.

The surfactants used in the composition of the present invention include polyethoxylate quaternary ammonium salts of long chain amines, particularly polyethoxylated quaternary ammonium nitrates of long chain mines.

Preferrably, the amines will have from 12 to 18 carbon atoms and these quaternary ammonium salts will contain 1 to 10 polyethoxylate groups. Also used in the practice of the present invention are mixtures of C12 to C14 alkyl mono-, di-, and tri- (alkyltetraglycol ether)-o-phosphates, known commercially under the name Hostaphat KL340N. The compositions of the present invention also include fatty acid esters of sorbitan, especially fatty acids of from 12 to 18 carbon atoms.

The surfactants are combined with the hydrocarbon solvent in a predetermined ratio sufficient to render a mixture of the aqueous phase and the hydrocarbon solution a liquid at a first temperature and a waxy solid at a lower second temperature. For example, the various surfactants and hydrocarbon solvent can be combined with the aqueous phase so as to provide a composition which at room temperature would be a waxy solid but at slightly above room temperature would be a liquid.

Typically, the amount of hydrocarbon liquid would be in the range of about 15 to about 40 weight % based on the total weight of the formulation.

The amount of fatty acids esters of sorbitan will typically be in the range from about 15 to about 40 weight % based on the total wt. of the second phase. The tetraglycol ether phosphates will be in the range of about 1 to 5 wt % and the polyethoxylated quaternary ammonium salts will be the range of about 12 to about 35 wt % based on the total weight of the second phase.

The aqueous phase containing the nitrogen and phosphorous nutrients will be present in the range of 25 to 55 weight % based on the total weight of the formulation.

In treating contaminated soil or water in accordance with the present invention, the temperature of the environment to be treated is first determined. Then a composition is selected which will comprise an aqueous solution of microbial nutrients in a first phase and a hydrocarbon second phase such that a mixture of the first and second phases will be a waxy solid at the temperature of the environment to be treated. The composition is then heated to a point where the mixture is a liquid and is applied, for example by spraying. The amount of composition that will be applied typically will depend on the weight percent of hydrocarbon contaminant on the soil or water. Preferably, the amount of formulation will be applied in amounts sufficient to provide a C:N:P ratio or from about 100:10:1 to about or about 100:1:0.1.

As will be apparent from the foregoing, the ability to apply the bioremediant in the liquid phase permits efficient and broad distribution to the contaminated environment. Because the compositions of this invention forms a waxy solid once applied, the nutrient remains bioavailable and is not readily leached in the water or ground being treated.

The following examples will more fully illustrate the invention.

EXAMPLES

Example 1

This example illustrates a range of compositions that form bi-continuous first and second phases. These compositions are shown in Table 1. Also shown in the table is the temperature at about which the second phase becomes a liquid.

Example 2

The usefulness of this invention for retarding the leaching of microbial nutrients from the surface to which it is applied is demonstrated in this Example 2. Two elution cylinders, each 1-¼ inch diameter by 8 inches long and fitted with a stopcock, were each packed with 200 g sand which had been intimately mixed with the following compositions:

Cylinder 1: 2.8 g of formulation A from Example 1 above, warmed to 35° C.

Cylinder 2: 4.0 g of a commercial liquid microbial nutrient product sold for its resistance to leaching from solid surfaces.

The above weights were chosen to deliver the same 0.64 g of urea to each cylinder. Distilled water in eight 25 ml aliquots was added dropwise at ~23° C. to each cylinder and the effluent was analyzed for urea spectrophotometrically. The results for Formulation A and the comparative commercial product ("Comp") are depicted in the FIGURE. The FIGURE demonstrates that formulation A shows a low tendency to leach out urea.

Example 3

Two separate pans of hydrocarbon contaminated soil 12 inches long by 8 inches wide and 3 inches deep were treated as described below. In pan 1, formulation A (Table 1) was heated to 30° C. and sprayed onto the soil at a quantity to provide a C:N:P ratio of 100:10:1. The soil was hand-tilled following the application. In pan 2 (control) no nutrients were applied to the soil. Both pans were watered and hand-tilled weekly. The amount of water applied was sufficient to provide a moisture content of about 17 wt. %.

After two-, four-, and six-week periods, the percent petroleum hydrocarbons biodegraded was determined for each of the examples using EPA method 418.1 with the following modifications:

1. The soil sample size was increased to 30 grams.
2. The acidification step specified in the test was eliminated.
3. The amount of drying agent required by the test was increased to assure effective drying.
4. The drying agent used was magnesium sulfate.
5. A four-hour time period for soxhlet extraction was employed.
6. The amount of silica gel used was increased.

Results of the soil biodegradation tests are shown in Table 2.

TABLE 1

WEIGHT % COMPONENTS

| Formulation | $C_{12}$ Ethaquad Nitrate | Hostaphat | Span20 | Norpar-13 | Urea | $NH_4H_2PO_4$ | Water | Solid to Liquid Transition Temp. (°C.) |
|---|---|---|---|---|---|---|---|---|
| A | 16.40 | 1.80 | 18.20 | 18.20 | 22.70 | 4.50 | 18.20 | 26 |
| B | 18.16 | 1.99 | 20.15 | 20.15 | 19.71 | 3.98 | 15.83 | 25 |
| C | 21.22 | 2.33 | 23.54 | 23.54 | 14.62 | 2.98 | 11.77 | 24 |
| D | 28.84 | 3.16 | 32.0 | 32.0 | 1.98 | 0.4 | 1.58 | 6 |

TABLE 2

| Soil Pan Identification | Treatment | % Hydrocarbon Degraded | | | |
|---|---|---|---|---|---|
| | | 2 wk. | 4 wk. | 6 wk. | 8 wk. |
| Pan 1 | Formulation A | 6.5 | 13.1 | 19.6 | 29.3 |
| Pan 2 | None | 0 | 2 | 1 | 1 |

What is claimed is:

1. A microbial nutrient composition comprising a mixture of a first phase and a second phase,
   the first phase being an aqueous phase of nitrogen and phosphorus microbial nutrients present in an amount ranging from about 25 to about 55 wt % based on the total weight of the composition, and
   the second phase being a paraffinic hydrocarbon liquid combined with from 15 to 40 wt % based on the weight of the second phase of fatty acid esters of sorbitan, 1 to 5 wt % based on the weight of the second phase of $C_{12}$ to $C_{14}$ alkyl mono, di, and tri (alkyltetraglycol ether)-o-phosphate, and from about 12 to about 35 wt % based on the weight of the second phase of polyethoxylated quaternary amonium salts of alkyl amines having from 1 to 10 polyethoxylate groups and alkyl amines of from 12 to 18 carbon atoms, thereby rendering the mixture of the first and second phase a liquid at a first temperature and a solid at a second lower temperature.

2. The composition of claim 1 wherein the aqueous solution includes urea and ammonium di-hydrogen phosphate.

3. The composition of claim 2 wherein the urea and ammonium di-hydrogen phosphate are in a weight ratio of about 5:1.

4. A method for enhancing the bioremediation of a hydrocarbon contaminated environment at an ambient temperature comprising:
   applying to the environment a composition that is a liquid at a first temperature and a solid at the ambient temperature, the composition comprising a first and a second phase, the first phase being an aqueous phase of nitrogen and phosphorus microbial nutrients present in an amount ranging from about 25 to about 55 wt % based on the total weight of the composition and the second phase being a paraffinic hydrocarbon combined with from 15 to 40 wt % based on the weight of the second phase of fatty acid esters of sorbitan, 1 to 5 wt % based on the weight of the second phase of $C_{12}$ to $C_{14}$ alkyl mono, di, and tri (alkyltetraglycol ether)-o-phosphate, and from about 12 to about 35 wt % based on the weight of the second phase of polyethoxylate quaternary ammonium salts of alkyl amines having from 1 to 10 polyethoxylate groups and alkyl amines of from 12 to 18 carbon atoms.

* * * * *